(12) United States Patent
Chang (10) Patent No.: US 11,123,125 B2
(45) Date of Patent: Sep. 21, 2021

(54) ORTHOPEDIC CLAMPS

(71) Applicant: Jonathan L. Chang, South Pasadena, CA (US)

(72) Inventor: Jonathan L. Chang, South Pasadena, CA (US)

( * ) Notice: Subject to any disclaimer, the term of this patent is extended or adjusted under 35 U.S.C. 154(b) by 121 days.

(21) Appl. No.: 16/351,417

(22) Filed: Mar. 12, 2019

(65) Prior Publication Data

US 2020/0289182 A1 Sep. 17, 2020

(51) Int. Cl.
*A61B 17/88* (2006.01)
*A61B 17/28* (2006.01)

(52) U.S. Cl.
CPC ........ *A61B 17/8866* (2013.01); *A61B 17/282* (2013.01); *A61B 2017/2808* (2013.01); *A61B 2017/2837* (2013.01)

(58) Field of Classification Search
CPC .......... A61B 2017/2808; A61B 17/282; A61B 2017/2837; A61B 17/808; A61B 17/88; A61B 17/8866; A61B 17/8872; A61B 17/8894; A61B 2017/90
See application file for complete search history.

(56) References Cited

U.S. PATENT DOCUMENTS

| | | |
|---|---|---|
| 5,797,919 A | 8/1998 | Brinson |
| 5,944,723 A | 8/1999 | Colleran et al. |
| 6,001,099 A * | 12/1999 | Huebner ................ A61B 17/80 606/280 |
| 6,315,780 B1 | 11/2001 | Lalonde |
| 8,685,037 B1 * | 4/2014 | Jordan ............... A61B 17/8866 606/105 |
| 9,011,507 B2 | 4/2015 | Schelling |
| 9,339,319 B2 | 5/2016 | Schmuck et al. |
| 9,532,825 B2 * | 1/2017 | Geebelen ............ A61B 17/1728 |
| 9,550,277 B1 | 1/2017 | Williams et al. |
| 9,642,641 B2 * | 5/2017 | Fernandez Dell'oca .................... A61B 17/808 |
| 9,675,400 B2 | 6/2017 | Katrana et al. |
| 9,730,741 B2 | 8/2017 | Makhlouf |
| 9,888,930 B2 | 2/2018 | Hänni et al. |
| 9,999,456 B2 | 6/2018 | Powell et al. |
| 2013/0116733 A1 * | 5/2013 | Stoll, Jr. ............... A61B 17/808 606/282 |

(Continued)

FOREIGN PATENT DOCUMENTS

| | | |
|---|---|---|
| CN | 205758659 | 12/2016 |
| CN | 106388925 | 2/2017 |

(Continued)

OTHER PUBLICATIONS

Bd V. Mueller Catalog, Williams-Style Discectomy Retractors NL5390-002, https://catalog1.bd.com/vmueller/williams-style-discectomy-retractors-nl5390-002.html, 2017, 2 pages.

(Continued)

*Primary Examiner* — Zade Coley
(74) *Attorney, Agent, or Firm* — Maceiko IP (57) ABSTRACT

An orthopedic clamp to assist in reducing the displacement between bone ends of a fracture, and to position a fixation device, during open fracture reduction surgery is described. The clamp includes a holder to hold the fixation device against the bone. The clamp may also swivel in relation to the holder while the position of the fixation device remains unchanged.

15 Claims, 6 Drawing Sheets

(56) References Cited

U.S. PATENT DOCUMENTS

2017/0209192 A1\* 7/2017 Krauss ............... A61B 17/8866
2017/0281283 A1 10/2017 Siegler et al.
2019/0328434 A1 10/2019 Slocum et al.

FOREIGN PATENT DOCUMENTS

| CN | 206836918 | 1/2018 |
|---|---|---|
| CN | 108078610 | 5/2018 |
| CN | 207492791 | 6/2018 |
| KR | 101681177 | 11/2016 |
| RU | 185903 | 12/2018 |

OTHER PUBLICATIONS

Bradshaw International, 25871 10" Deluxe Tongs, https://www.amazon.com/BRADSHAW-INTERNATIONAL-25871-Deluxe-Tongs/dp/B000BPBT7M, 2018, 10 pages.

Innomed, Inc., Foot & Ankle Instruments, Innomed Small Bone Instruments—Foot & Ankle-Bone Clamps, 2019, 18 pages.

\* cited by examiner

ORTHOPEDIC CLAMPS

FIELD OF THE INVENTION

The current invention generally relates to devices and techniques to facilitate orthopedic surgeries, including clamps and devices for use in open fracture reduction surgery to maintain a reduction, provide alignment and/or to position an internal fixation device during surgery.

BACKGROUND OF THE INVENTION

When a bone is fractured, the broken bone ends and/or or other parts of the bone may become displaced. When the displacement is significant, surgery is often necessary to directly access the broken bone ends and/or other bone pieces, so that the fracture may be reduced, and so that an internal fixation device, such as a plate, may be attached to broken bone ends and/or other bone pieces to hold them in place while the bone heals.

In open reduction surgery, various clamps and other devices have been used to reduce the fracture and align the broken bone ends and/or other bone pieces so that they are in proper position prior to attaching the internal fixation device. However, while existing clamps may be effective in reducing the fracture, they do not aid in attaching the plate or other internal fixation device. Furthermore, existing clamps must typically be removed when the internal fixation device is installed, because otherwise the clamp would be in the way of where the internal fixation device would be installed, or would otherwise interfere with installation.

As a result, a surgeon must typically remove the reduction clamps so that the internal fixation device may be installed. This often requires the surgeon to maintain the reduction by hand. For example, the surgeon holds the broken bone ends together by hand while a plate is attached to the broken bone ends with screws.

This generally results in a suboptimal process because the reduction may not be fully maintained by the surgeon and/or the alignment of the broken bone ends may not be maintained in an optimal position. This process may also lengthen the duration of the surgery which is also suboptimal because it is preferred to reduce the time that a patient is under anesthesia.

Certain existing clamps have attempted to hold a plate in place. However, such clamps had fixed angles and/or had a small footprint such that they would rarely accommodate or fit a plate; and even if they did, they would not securely hold the plate but would instead allow it to rotate or otherwise move from its desired position. Furthermore, such clamps have typically not been intended for fracture reduction. Other existing clamps that have attempted to hold a plate in place have also involved additional components, such as temporary fixing plates, that may tend to make the overall open fracture reduction surgery more complicated and/or longer.

Some of these other existing clamps are very invasive and would require excessive dissection of the tissue surrounding the fracture. Other existing clamps would simply be too large or cumbersome to use for open fracture reduction surgery.

Accordingly, there is a need for a surgical device that facilitates open reduction surgery by assisting in the reduction of fractures and the placement and installation of internal fixation devices. There is also a need for a more efficient process of performing open reduction surgery.

SUMMARY OF THE INVENTION

An aspect of the invention is that the surgical clamp may be used to reduce a fracture, and to maintain the reduction, while also including a plate holder, or frame, to hold the plate or other internal fixation device in place for installation. This is a significant advance because with the clamp of the current invention, a reduction may be more easily and accurately maintained, and the reduction need not rely on the surgeon maintaining the reduction by hand. This is also a significant advance because reduction clamps, unlike those currently existing, need not be removed.

Another aspect of the invention is that different sizes and shapes of plates and other internal fixation devices may be held in place by the clamp. To accommodate different shapes and sizes, the frame of the plate holder may comprise rectangles and other shapes of different sizes. The frame may also be curved to accommodate holding a curved plate in place. It is preferred that the frame be sized so as to securely hold the plate or other internal fixation device, e.g., to avoid wiggle room or rotation of the plate relative to the frame.

Another aspect of the invention involves the frame having a window or cutout that provides access to the bone where the screws or other attachment means will be installed. As such, the clamp of the current invention allows the installation of screws while holding the internal fixation device in place, and also while maintaining the reduction. In an alternative embodiment, the window or cutout may be solid material with holes cutout to correspond to where the screws or other attachment means will be installed to secure the plate to the bone.

Another aspect of the invention involves the tool having a swivel between the plate holder and the rest of the tool. This allows the surgeon to swivel the frame of the plate holder to the desired orientation along the bone, while holding the tongs of the tool in the same place, thereby allowing the surgeon to better maintain the reduction. In an alternative embodiment, the plate holder may be fixedly attached to the tool. While the adjustability of a swivel does not exist in this embodiment, the fixed configuration may be suitable for surgery where the tool is generally held at a certain angle.

Other aspects of the invention render the device easier to use during surgery. For example, the tool of the current invention preferably includes a ratchet mechanism to lock or otherwise hold the tongs in the desired position. In this manner, pressure may be exerted on opposite or different directions on the bone(s) thereby maintaining the reduction and freeing up the surgeon to perform other tasks in the surgery.

Another aspect of the invention involves making an open reduction surgery more efficient. For example, reduction clamps need not be removed so that the internal fixation device may be installed. And time is not spent ensuring that the reduction is properly maintained by the surgeon's hand before and during installation of the internal fixation device. Time is also not spent manipulating additional components, such as temporary plates. As such, the duration of the surgery, and the amount of time that the patient is under anesthesia, may be reduced. The surgery may also be rendered less complicated thereby making the surgery more of an optimal situation.

The current invention may also make the surgery more efficient by aiding in the retraction of the skin to provide access to the fracture. That is, the clamp of the current invention allows for an upright placement on the fractured bone that may help retract the skin, which in turn, may avoid the need for a separate skin retractor during surgery. As such, the surgeon may perform the surgery while having to position and/or manipulate fewer surgical tools, which may decrease the time of surgery. Furthermore, a person who would otherwise be required to assist in the surgery by manipulating the skin retractor may be unnecessary.

Other aspects of the invention are discussed herein.

DETAILED DESCRIPTION OF THE PREFERRED EMBODIMENTS

Figure 1:
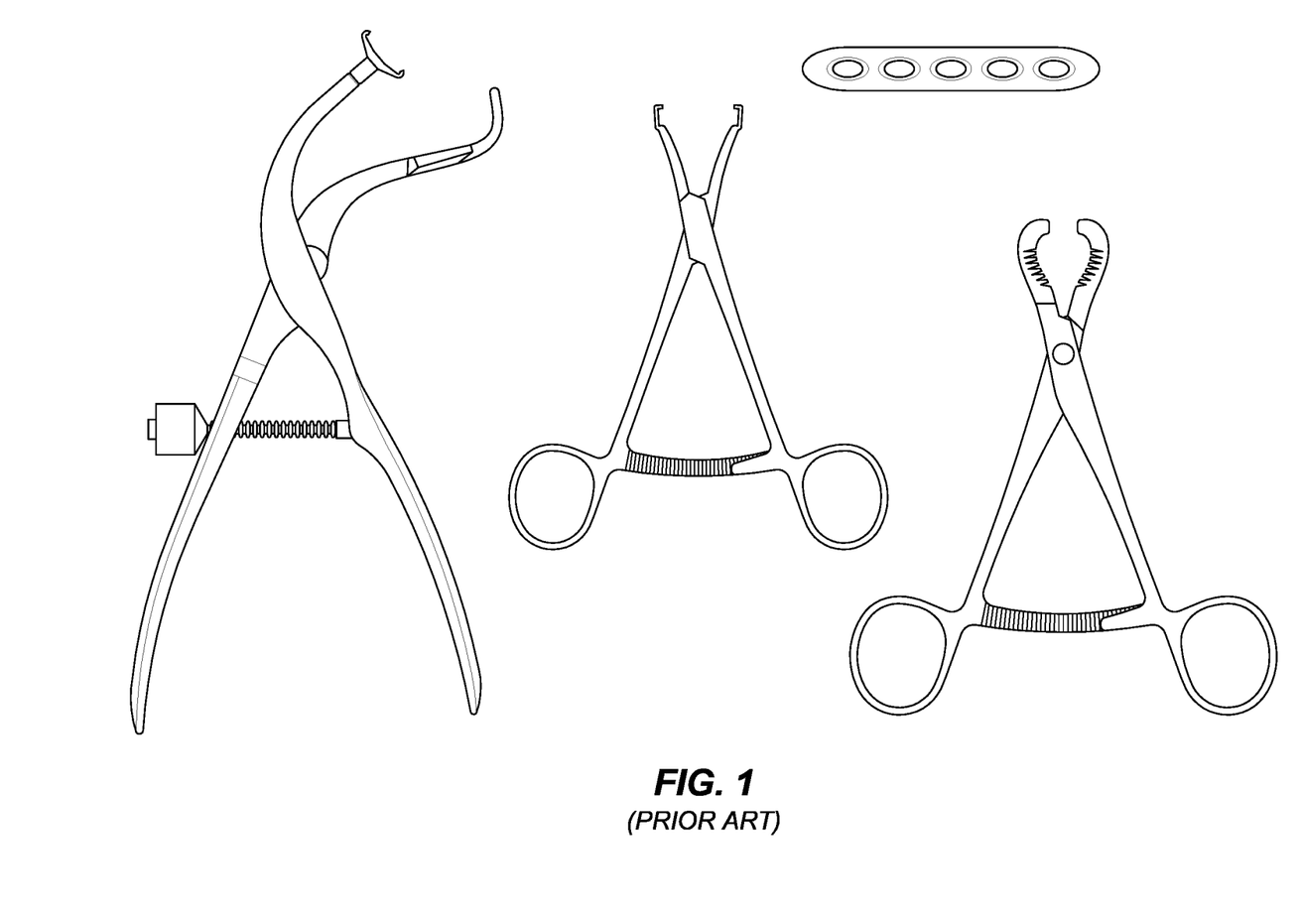
FIG. 1 is a picture showing existing fracture reduction clamps and an internal fixation device comprising a plate.

The current invention is now described with reference to the figures. FIG. 1 shows several existing types of clamps, as well as an existing internal fixation plate. Generally, the existing clamps may be used to reduce the fracture, and maintain the reduction, but at least one of the tongs will be in the way of installing the plate. Accordingly, these existing clamps must typically be removed in order to install the plate.

As noted above, this requires the surgeon to maintain the reduction by hand while also positioning the plate and holding the plate in place while installing the screws or other attachment means used to fix the plate before the patient is closed. This is a suboptimal process because the integrity of the reduction or the alignment of the broken bone ends or other bone pieces may be lost or reduced. This is also a suboptimal process because it is inefficient and may increase surgery time and the time that the patient is under anesthesia.

Referring to FIGS. 2-5, the current invention is now described in more detail. Orthopedic clamp or device or tool 10 may include first or lower tong 20 and second or upper tong 30 that may be moveably coupled to each other. First or lower tong may include distal or tong end 22 which, when tool 10 is used, may engage the bone being reduced and may serve to press from a first direction, e.g., the underneath or the bottom of a reduction, or the distal side of the reduction located away from the surgeon. Tong end 22 may include serrated section 22A to help it securely engage the bone to be reduced.

Distal or tong end 22 may comprise a curved and/or tapered end, which allows it to be placed on the distal, opposite or other side of the bone to be reduced and plated without needing to dissect more soft tissue around or from that side of the bone. This may generally improve the healing potential of the fracture.

In an alternative embodiment, distal or tong end 22 may be configured to include a rectangular or curved piece that may support more of a length of the distal, underside or other side of the bone(s). Lower tong 20 may also include a handle having a finger hole 24 and positioning or locking stem 26. Stem 26 may include a series of ridges, peaks/valleys or teeth 26A, 26B, etc.

Second or upper tong 30 may include distal or tong end 32, and a handle having finger hole 34 and positioning or locking tab 36. Tab 36 may include one or more ridges or high points 36A, 36B, etc. that may engage with the teeth 26A, 26B, etc. of stem 26 to lock the tool 10 in a desired configuration. Tongs 20, 30 may be moveably coupled to each other or joined by a threaded screw arrangement or other form of attachment 40 that preferably allows tongs 20, 30 to move or rotate relative to each other about attachment 40. In a preferred embodiment, stem 26 and tab 36 comprise a ratchet to lock or hold tongs 20, 30 in the desired position once determined by the surgeon.

The distal end 32 of upper tong 30 may interface with holder, insert or cutout assembly 50 that may be configured to hold or position a plate or other fixation device in the location at which it will be attached to the fractured bone(s).

Figure 6:
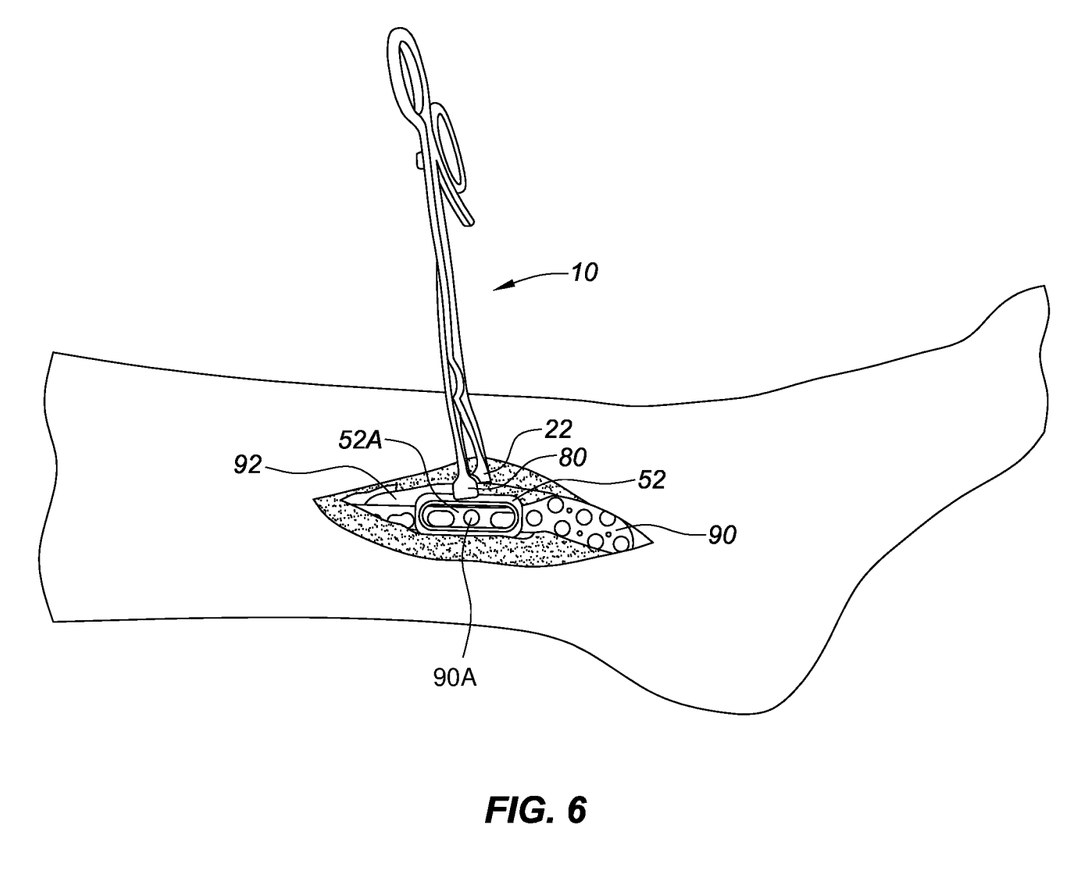
FIG. 6 shows a clamp and fixation device holder during surgery.

Holder 50 may include frame or cutout 52 that may be attached to tong end 32 via swivel 80. Frame 52 may generally serve to position the plate 90 (as shown in FIG. 6) or other internal fixation device, as well as to hold plate 90 in place on bone 92 while screws or other attachment means are installed. That is, plate 90 may be held between frame 52 and the bone 92 so that tool 10 presses plate 90 towards the bone 92 in the desired location so as to securely hold it in place. In this manner, when the surgeon squeezes tong handles 24, 34 together, frame 50 and distal end 22 exert forces in opposite or other directions towards each other which serves to maintain the reduction and hold plate 90 in place for installation.

In this manner, the current invention represents an advance over certain existing tools that may provide a socket in which to position the plate, e.g., the device shown at the link below:

http://www.innomed.net/ smallbone_footankle_clamps.htm#DuncanClampFt

However, in those existing tools, the plate merely rests on top of the tool and is not clamped between the tool and the bone. As such, the plate is not securely held in place with respect to the bone. Furthermore, in these existing tools, the plate may rotate or wiggle relative to the tool which further adds to issues because the plate is not securely held in place.

Figure 2:
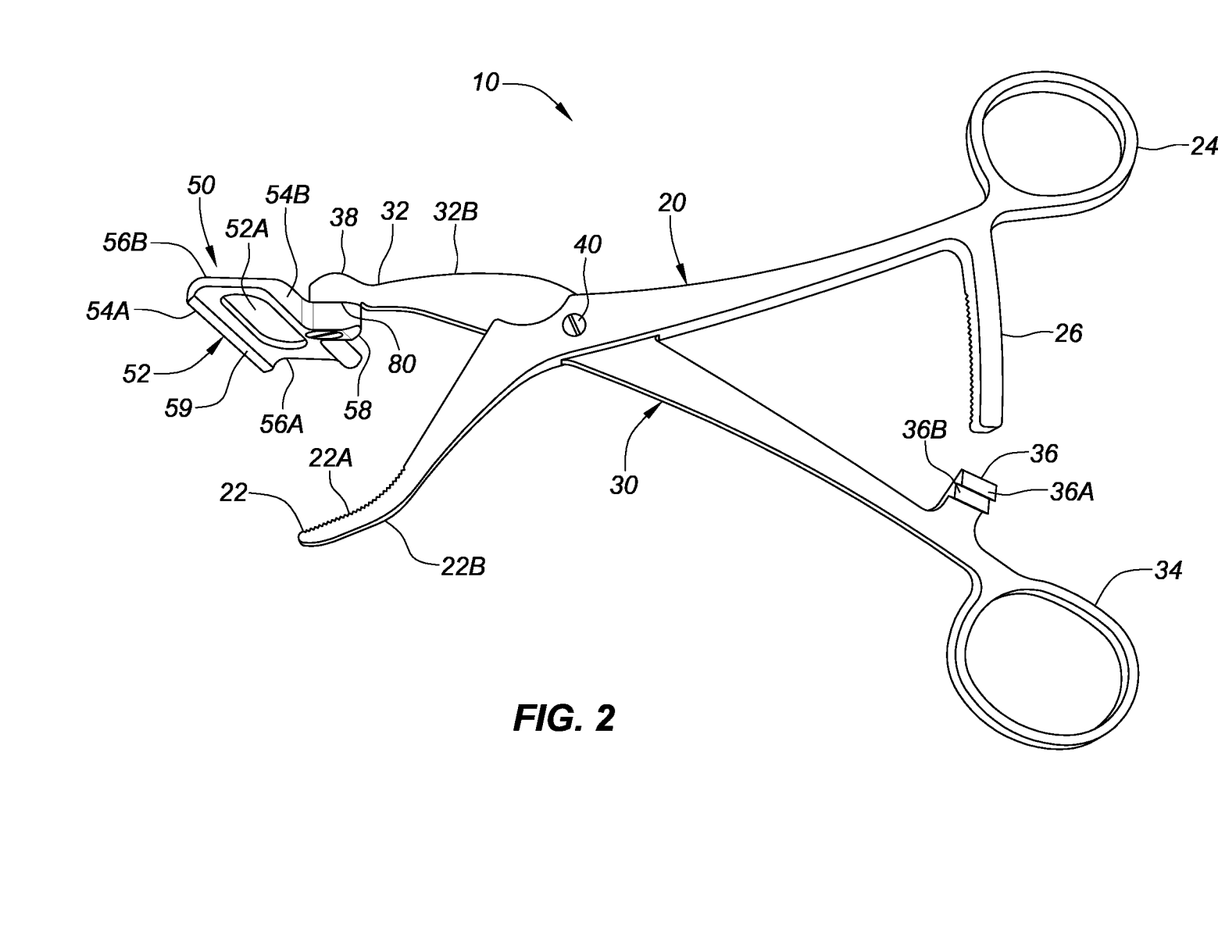
FIG. 2 is a side perspective view of a clamp and fixation device holder.
Figure 4:
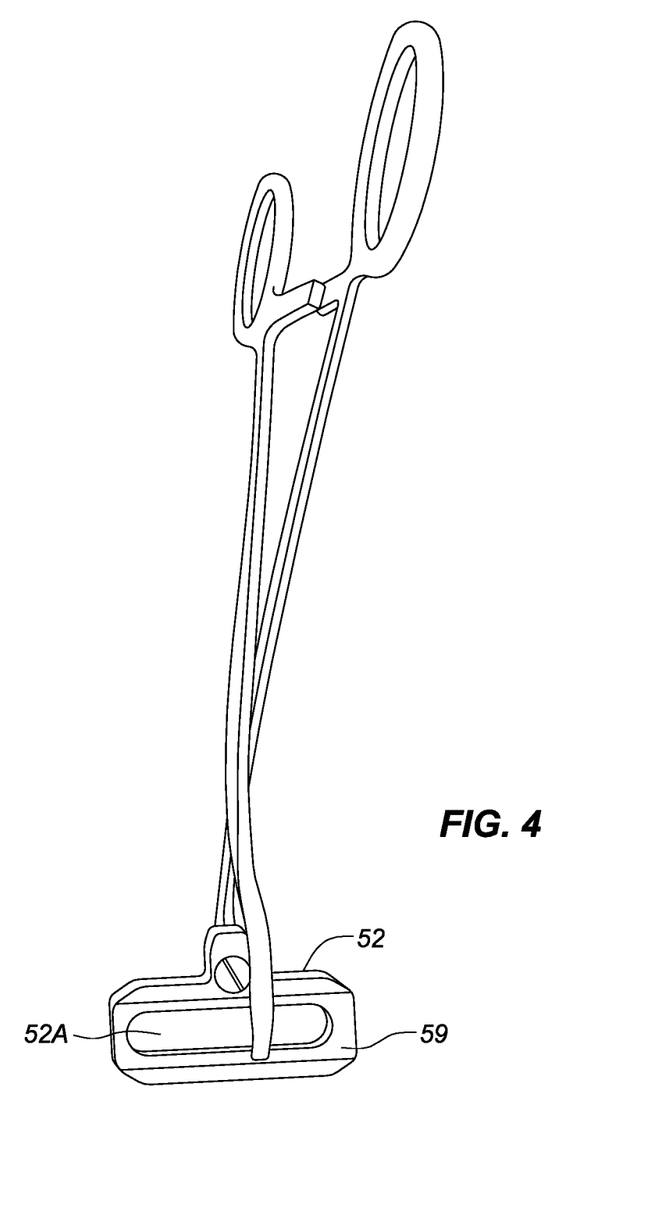
FIG. 4 is a rear perspective view of a clamp and fixation device holder.
Figure 5:
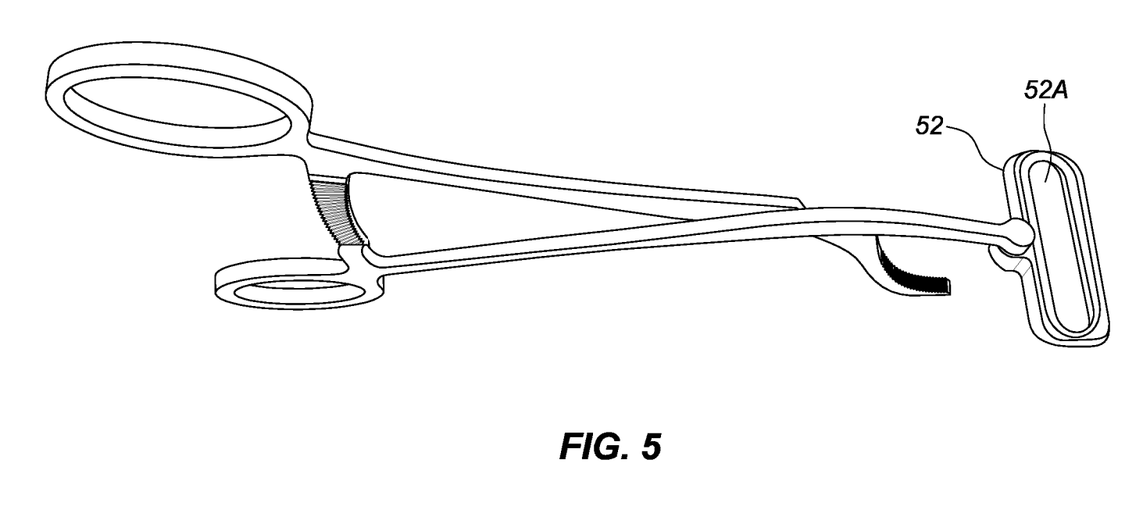
FIG. 5 is a front perspective view of a clamp and fixation device holder.

To facilitate the swiveling of frame 52 relative to upper tong 30, tong end 32 may include threaded hole 38 and plate holder assembly 50 may include tab 58. The swivel 80 attachment between tab 58 and hole 38 may comprise a bolt or screw (as shown in FIGS. 2 and 4), bearing, bushing or other attachment mechanism that allows frame 52 to swivel relative to upper tong 30. It is preferred that the attachment mechanism allows the smooth swiveling of frame 52 relative to tong 30 so that tool 10 may be swiveled without disrupting the position of plate 90. As discussed in more detail later, the swiveling capability allows clamp 10 to maintain the reduction while allowing the surgeon a degree of freedom in placing the plate or other internal fixation device, and to perform other tasks such as installing the screw to attach the plate to the bone(s).

Frame 52 may be configured to accommodate various shapes and sizes of plates or other internal fixation devices. It is preferred that frame 52 engage at least some of the edges of the plate while providing access to the upper surface of the plate, i.e., it is preferred that frame 52 surround a "window" or opening 52A that allows access to the part of the plate within the perimeter of frame 52 as it engages the reduced bone ends. This allows the surgeon to install screws or other attachment means within window 52A and through the plate and into the bone. Additionally, frame 52 securing plate 90 to the bone(s) also allows the surgeon to install screws outside the perimeter of frame 52.

In the embodiment of tool 10 shown in FIGS. 2-5, frame 52 may be shaped as a rectangle comprising sides 54A, 54B and ends 56A, 56B. This configuration may be preferred for a fibular fracture reduction. The lengths of sides 54A, 54B and/or the ends 56A, 56B may be varied to accommodate different sized rectangular plates. However, frame 52 may comprise other shapes and sizes. Furthermore, frame 52 may be curved in both the longitudinal and/or transverse dimension(s) to accommodate curved plates or other internal fixation devices. Accordingly, tool 10 of the current invention is not limited for use with fibular fractures. Indeed, clamp 10 of the current invention may be used for open reduction surgeries on a number of other bones with their own particular shapes, sizes and/or configurations.

Figure 3:
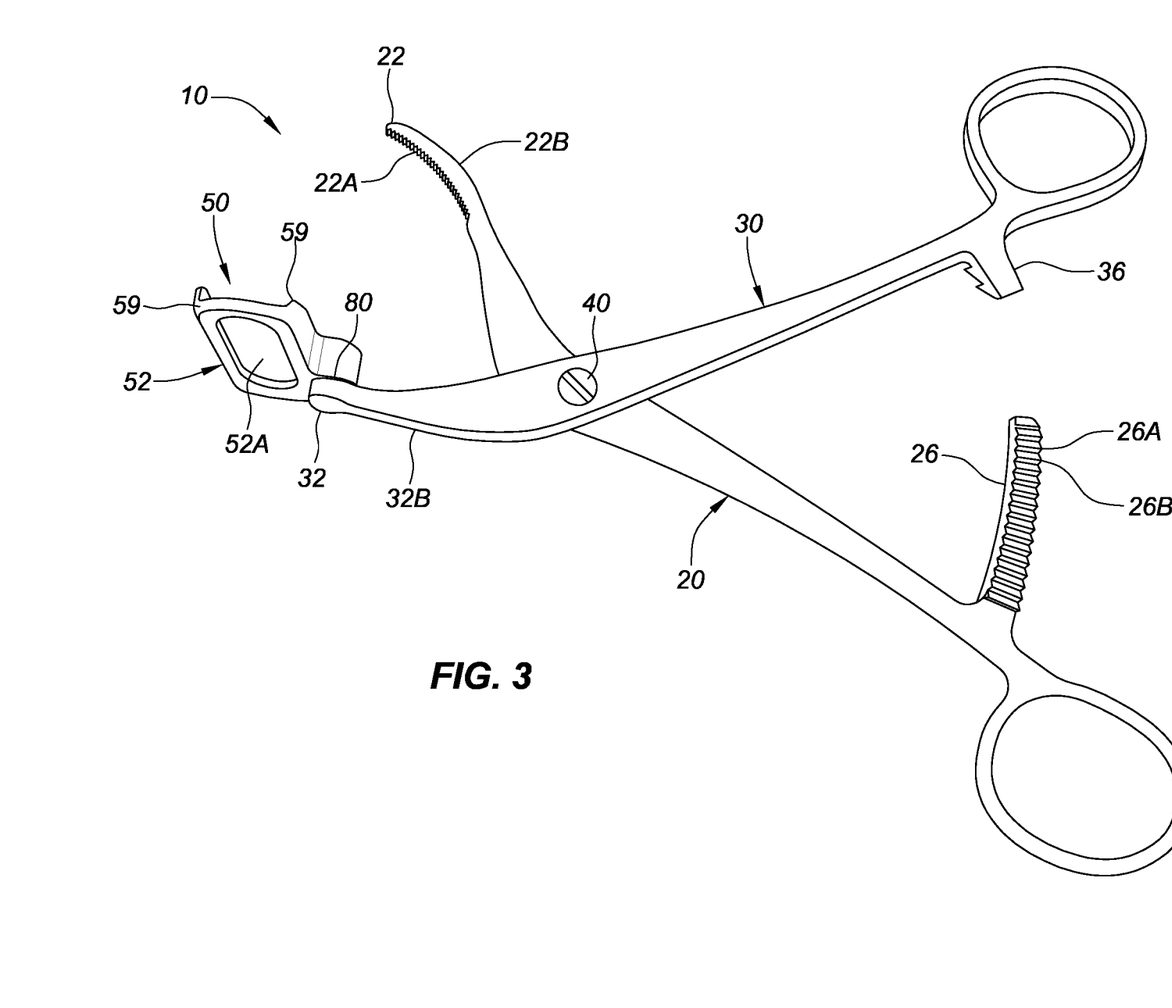
FIG. 3 is a side perspective view of a clamp and fixation device holder.

As best shown in FIGS. 2-4, frame sides 54A, 54B may extend downward to form lip 59 that may help contain and position the plate to be installed. This is in addition to the fact that tool 10 pushes the plate towards the bone(s). As such, tool 10 provides a secure placement and positioning of the plate unlike prior devices.

In the embodiment shown in FIGS. 2-5, frame ends 56A, 56B do not have lip 59, and the plate to be installed may extend beyond frame 52. However, in other embodiments, lip 59 may extend around the periphery of frame 52 thereby providing a "socket" type holder for the plate being installed.

Beyond the unique and innovative characteristics of tool or clamp 10 described above, the current invention also provides for a safer, more accurate and more efficient way to conduct an open fracture reduction surgery. To this end, the current invention fills an unmet need for a device that may reduce the fracture, and then better maintain the fracture reduction while also holding the repair plate or other fixation device in its proper position at the same time without having to remove the reduction clamps. As noted above, this may generally eliminate the human aspect of maintaining the reduction by hand, which may lead to misalignment and also prolong the length of the surgery and the time the patient is under anesthesia.

Furthermore, the swiveling 80 of holder or frame 52 with respect to tong 30 preferably holds the plate against the bone while the angled opposite tip 22 allows for positive tightening without the need for any further soft tissue dissection. By holding onto the plate itself, the reduction will not be lost while positioning the properly sized plate on the reduced fracture, and window 52A also allows for drilling of multiple holes in the plate under frame 52 without moving clamp 10. This improves upon current available equipment that does not allow any of these maneuvers to occur.

FIG. 6 shows tool 10 in use during an open fracture reduction surgery of a fractured bone, e.g., fibula 92. As shown, tool 10 is positioned in the desired location to both reduce the fracture and locate the plate or other fixation device for installation. Once tool 10 is thus positioned, the ratchet mechanism 26, 36 holds tongs 20, 30 in a fixed position relative to each other.

As also shown in FIG. 6, distal or tong end 22 helps maintain reduction of the fracture by pressing it towards the surgeon from the other side of the bone. Because distal or tong end 22 may be configured as a tapered and pointed end, it can be seen how further dissection of the tissue around the fibula need not be further dissected, which would be the case if tong end 22 were configured with a transverse piece (that would be axially aligned with the fibula).

The current invention may also make the surgery more efficient by aiding in the retraction of the skin to provide access to the fracture. That is, the clamp 10 of the current invention allows for an upright placement on the fractured bone 92 that may help retract the skin, which in turn, may avoid the need for a separate skin retractor during surgery. To this end, the section or strut 22B of tong 20 that may be positioned on the distal side of the reduced fracture may be in contact with, and help retract, the skin on that side of the incision that may help avoid the need for a separate skin retractor. Similarly, the section or strut 32B of tong 30 may also help retract the skin when it is in contact with the skin.

As such, the surgeon may perform the surgery while having to position and/or manipulate fewer surgical tools, thereby decreasing the time of the surgery. Furthermore, an assistant who would otherwise be required to manipulate the skin retractor may be unnecessary.

Frame 52 preferably secures plate 90 against the fractured bone, e.g., fibula 92. As shown, window or cutout 52A provides ready access to plate 90 and plate holes 90A through which screws or other attachment means may be installed. In addition, frame 52 holds plate 90 in place while plate holes 90A outside of frame 52 are also accessible.

The unique benefit of swivel 80 is also shown in FIG. 6. That is, once frame 52 and plate 90 are located in the desired position, swivel 80 allows tool 10 to be rotated relative to frame 52 without moving plate 90. To this end, it is preferred that the swivel connection 80 allows the smooth and/or unhindered rotation of tool 10 relative to frame 52 and plate 90 so that plate 90 may remain in the desired located while tool 10 is swiveled. The smooth swiveling operation may be provided by a bearing, bushing, nut/bolt or other suitable mechanisms. Maintaining the position of plate 90 while swiveling tool 10 may be desired especially where screw holes may have been drilled into the bone to be plated, and it is optimal for plate 90 to remain in the position so that the screw holes in plate 90 match up with screw holes drilled into the bone.

The swiveling capability of tool 10 may also be facilitated by distal or tong end 22B being tapered or pointed, because the tip of distal end 22 may contact the bone and still rotate relative thereto without cutting into any surrounding tissue and/or requiring any further dissection. The swiveling capability of tool 10 is beneficial, for example, to provide more space for the surgeon to install the screw and to manipulate the tools necessary to do so.

The frame 52 and its lip 59 are preferably configured in a curved fashion, i.e., curved along its ends 56A, 56B to correspond to and better hold a curved plate 90 that is, in turn, configured to generally correspond to the curvature of the fibula or other bone to be plated. Furthermore, the foregoing may all occur while tool 10 maintains the fracture reduction and does not require removal of reduction clamps and/or require the surgeon to maintain the reduction by hand while installing the plate 90. To this end, the locking ratchet connection 26, 36 may keep tongs 20, 30 in the desired locked position so as to maintain pressure from opposite or different directions against the bone(s). In this manner, the reduction is maintained while the surgeon is free to concentrate on the tasks associated with fixing plate 90 to the bone(s).

Although certain presently preferred embodiments of the invention have been described herein, it will be apparent to those skilled in the art to which the invention pertains that variations and modifications of the described embodiments may be made without departing from the spirit and scope of the invention.

What is claimed is:

1. A device to assist in surgery, comprising:
a first tong that includes a distal end which is configured to engage a fractured bone;
a second tong that includes a distal end, and that is moveably coupled to the first tong; and
a holder that is moveably coupled to the distal end of the second tong and that is configured to position a fixation plate between the holder and the fractured bone, and in contact with the fractured bone prior to installation of a bone screw or other attachment device,
wherein the holder includes a frame surrounding an opening which provides access to the fixation plate, and
wherein the frame is sized to engage edges of the fixation plate.

2. The device of claim 1, wherein the frame includes two sides and two ends, and wherein the two sides form lips that engage two edges of the fixation plate.

3. The device of claim 2, wherein the two ends form lips that engage two other edges of the fixation plate.

4. The device of claim 1, wherein the holder is curved.

5. The device of claim 1, wherein the holder applies pressure to the fixation plate against the bone in a first direction, and the distal end of the first tong applies pressure to the bone in a second direction.

6. The device of claim 1, wherein the distal end of the first tong is tapered so to avoid dissection beyond that required for the distal end of the first tong to be placed against the bone.

7. The device of claim 1, configured to position the fixation plate on a fractured fibula.

8. A device to assist in surgery, comprising:
a first tong that includes a distal end which is configured to engage a fractured bone;
a second tong that includes a distal end, and that is moveably coupled to the first tong;
a holder that is moveably coupled to the distal end of the second tong by a swivel and that is configured to position a fixation plate between the holder and the fractured bone, and in contact with the fractured bone prior to installation of a bone screw or other attachment device.

9. A device to assist in surgery, comprising:
a first tong that includes a distal end which is configured to engage a fractured bone;
a second tong that includes a distal end, and that is moveably coupled to the first tong;
a holder that is moveably coupled to the distal end of the second tong and that is configured to position a fixation plate between the holder and the fractured bone, and in contact with the fractured bone prior to installation of a bone screw or other attachment device; and
a ratchet that is configured to lock the first tong and the second tong in a locked position.

10. The device of claim 9, wherein the first tong and the second tong are held in the locked position by the ratchet, and the device is rotated relative to the holder about a swivel.

11. An orthopedic clamp for assisting with open fracture reduction surgery, comprising:
a first tong that includes a distal end which is configured to engage a fractured bone;
a second tong that includes a distal end and that is moveably coupled to the first tong;
a frame that is rotatably coupled to the distal end of the second tong by a swivel, that is configured to position a fixation plate between the frame and the fractured bone, and in contact with the fractured bone prior to installation of a bone screw or other attachment device, and that includes at least one lip to engage an edge of the fixation plate.

12. The orthopedic clamp of claim 11, wherein the first tong includes a first handle and the second tong includes a second handle, and wherein the distal end of the first tong and the frame maintain a reduction of the fractured bone when the first handle and second handle are squeezed together.

13. The orthopedic clamp of claim 12, further comprising a ratchet mechanism to lock the first tong and the second tong in a desired position.

14. The orthopedic clamp of claim 13, wherein the first tong and second tong are rotated about the swivel in relation to the frame.

15. The orthopedic clamp of claim 11, wherein the frame is curved.

* * * * *